United States Patent [19]

Lalin

[11] Patent Number: 4,532,814
[45] Date of Patent: Aug. 6, 1985

[54] FLUID SAMPLER AND GAS FLOW CONTROL SYSTEM AND METHOD

[76] Inventor: Hill S. Lalin, 10 Bonita Ter., Wayne, N.J. 07470

[21] Appl. No.: 512,935

[22] Filed: Jul. 12, 1983

[51] Int. Cl.³ .............................................. G01N 1/24
[52] U.S. Cl. ............................... 73/863.03; 73/863.21; 73/863.23; 73/864.34
[58] Field of Search ........... 73/863.03, 863.02, 863.01, 73/863.21, 863.22, 863.23, 863.24, 863.25, 864.34; 55/270; 417/307, 309, 311

[56] References Cited

U.S. PATENT DOCUMENTS

| | | | |
|---|---|---|---|
| 2,693,114 | 11/1954 | Tapp et al. | 73/863.02 |
| 2,819,774 | 1/1958 | Schmidt et al. | 55/270 X |
| 2,982,131 | 5/1961 | Rosinski | 73/863.23 X |
| 3,343,217 | 9/1967 | Daubenberger | 417/311 X |
| 3,501,899 | 3/1970 | Allen | 55/270 X |
| 3,689,197 | 9/1972 | Berle et al. | 417/307 X |
| 3,965,747 | 6/1976 | McCorkle | 73/863.02 |
| 4,140,436 | 2/1979 | Schumacher et al. | 417/311 X |
| 4,246,788 | 1/1981 | Olin et al. | 73/863.03 |
| 4,269,059 | 5/1981 | Baker | 73/863.03 |
| 4,432,248 | 2/1984 | Lalin | 73/863.03 |

FOREIGN PATENT DOCUMENTS 709977  1/1980  U.S.S.R. ............................ 73/864.34

*Primary Examiner*—Stewart J. Levy
*Assistant Examiner*—Tom Noland

[57] ABSTRACT

The fluid Sampler is used to sample gases in a collecting device and includes a flow control valve having a manually adjustable flow restricting orifice and a vacuum pump for drawing gas from the atmosphere through the collecting device and flow control valve to form therethrough a primary flow path. A flow controller is used to supply a supplemental flow of gas taken from the discharge end of the vacuum pump and supplied to the suction end of the vacuum pump in response to the differential in pressure across the flow control valve. The supplementary flow rate is automatically adjusted to maintain the differential in pressure constant.

17 Claims, 5 Drawing Figures

FLUID SAMPLER AND GAS FLOW CONTROL SYSTEM AND METHOD

This invention relates to a fluid sampler for sampling gases particularly air and to a pneumatic flow control system and method for maintaining a constant rate of gas flow through a load at a preselected flow rate within a wide flow range substantially independent of variations in the load.

BACKGROUND OF THE INVENTION

In the field of environmental hygiene air sampling is performed regularly to test the air in industrial work environments to determine the degree of exposure to hazardous chemicals. A typical sampling method involves collecting a sample of a test gas such as air by drawing a known volume of the test gas through a collecting device such as a sorbent tube. The sorbent tube may include a solid adsorbent capable of trapping and removing chemicals from the air or may include a filter for selectively collecting particulates. The test sample is then analyzed to determine the concentration level of the collected sample of chemicals or particulate matter. The method of analysis may involve gas chromatography or atomic adsorption, etc. The analysis is based on a time weighted average over an eight hour work day to determine the concentration level of contaminants in parts per million. For the analysis to be accurate it is essential that sampling of test gas be performed at a constant fluid flow rate which is preselected for the chemical hazard under examination.

Chemical sampling, i.e., sampling of gases or vapors, is typically conducted at low flow levels in a flow range typically between 1 to 250 cc per minute depending upon the chemical hazard under analysis. In the sorbent tube sampling method air is drawn through the sorbent tube by a vacuum pump at a flow rate which must be held constant to assure accurate results. One currently used technique to assure constant flow is to use a pump and counter in conjunction with a precalibrated known volume of test gas from which the total volume can be derived. This technique is nonetheless susceptible to erroneous results from changes in back pressure as a result of changes in pump volumetric efficiency, valve loading, etc. In another type of pump sampling system air flow is controlled by adjustment of the pump motor speed. One conventional system uses a pressure switch to generate output pulses which vary in duration corresponding to variations in flow rate. The pulsed output is electronically sensed and converted to control signals having an amplitude which varies with pulse duration. The control signals are then used to adjust the pump motor speed. Another known motor speed control system utilizes load sensing of the pump motor to adjust motor speed in proportion to the pump load line curve. The latter motor speed control system is shown and described in Applicant's earlier U.S. Pat. No. 4,432,248 issued February 1984. All known pump sampling systems which control flow by adjustment of pump motor speed produce an air flow with relatively high pulse undulations particularly at low flow levels. With a highly pulsed flow it is difficult to set the flow rate. In fact at very low flow rates of the order of 10 cc per minute or below a flow meter cannot be used to determine and calibrate the flow rate. Accordingly, at flow conditions it is still the practice to use a number of different pump systems to cover the low flow range with each calibrated to regulate flow in a very limited flow range.

SUMMARY OF THE INVENTION

The system of the present invention operates on a concept entirely different from the state of art in that flow is controlled independently of the operating speed and substantially independently of the pump characteristics. Gas flow is regulated in accordance with the present invention by regulating the differential in pressure across a metering orifice through which a primary gas stream flows and applying such differential to a flow controller having a valve assembly which regulates a supplementary flow of gas supplied to the pump inlet. The supplementary flow is combined with the primary gas stream at the pump inlet so as to maintain the differential in pressure across the metering orifice constant thereby controlling primary flow rate and at the same time the flow demand at the pump. In accordance with the theory of the present invention, as long as this differential in pressure is maintained constant, the primary gas stream flow, which represents the flow through the metering orifice, will be constant. Any pressure drop across a test load such as the sorbent tube in series with the metering orifice will have a minor effect on the flow. Accordingly, the system will automatically compensate for any change in test load to assure a constant flow rate over the duration of the test and without requiring recalibration each time a new test sorbent tube is introduced into the system. The flow rate is established by adjustment of the metering orifice to a desired flow setting within a wide flow range.

OBJECTS AND BRIEF DESCRIPTION OF THE DRAWINGS

It is therefore the principle object of the present invention to provide a fluid sampler for sampling gases including a gas flow control system and method for regulating the flow of gas through the fluid sampler at any preadjusted flow rate within a very wide flow range substantially independent of load conditions.

It is another object of the present invention to provide a pneumatic gas flow control system and method for regulating gas flow through a load at very low gas flow rates substantially independently of variations in the load.

Other objects and advantages of the present invention will become apparent from the following detailed description of the invention when reading in conjunction with the accompanying drawings of which:

DESCRIPTION OF THE PREFERRED EMBODIMENT(S)

Figure 1:
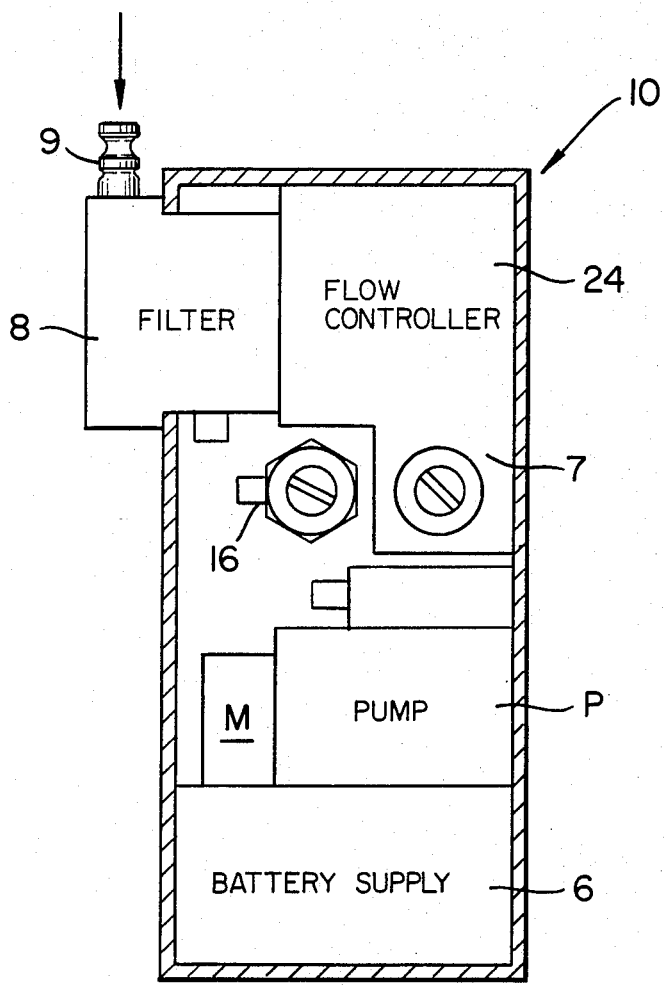
FIG. 1 is a full scale side elevation of the air sampler of the present invention.

Referring now to FIGS. 1-4 illustrating the fluid sampler and gas flow control system of the present invention. The fluid sampler 10 consists of a vacuum pump P, a DC motor M, a battery supply system 6, a flow control valve 16, a flow controller 24, a pressure switch 7 and a filter assembly 8. The filter assembly 8 has an air intake boss 9 mounted on the outside of the case and a filter membrane (not shown) to protect the pump P from dirt and debris. The pump P may be a single or dual piston diaphragm type pump preferably with preloaded valving as disclosed in applicant's corresponding U.S. Pat. No. 4,432,248, entitled Fluid Sampling, the disclosure of which is herein incorporated by reference. The pump P is driven by the DC motor M which is powered by the battery supply system 6. The battery supply system 6 may consist of a nickel cadmium battery assembly and may further include a battery voltage indicator and timer to indicate hours of operation.

A collecting device (not shown), such as a sorbent tube for taking gas samples, preferably of air, is coupled to the inlet boss 9 of the fluid sampler 10. A sorbent tube is a cylindrical shaped vial normally filled with a solid adsorbent or charcoal filter which is sealed at both ends with breakable end tips. The end tips are broken open when collecting an air sample. The pump P draws air through the sorbent tube at a fixed preset rate as determined by manual adjustment of the flow control valve 16. The flow rate is monitored and regulated by the flow controller 24.

Figure 2:
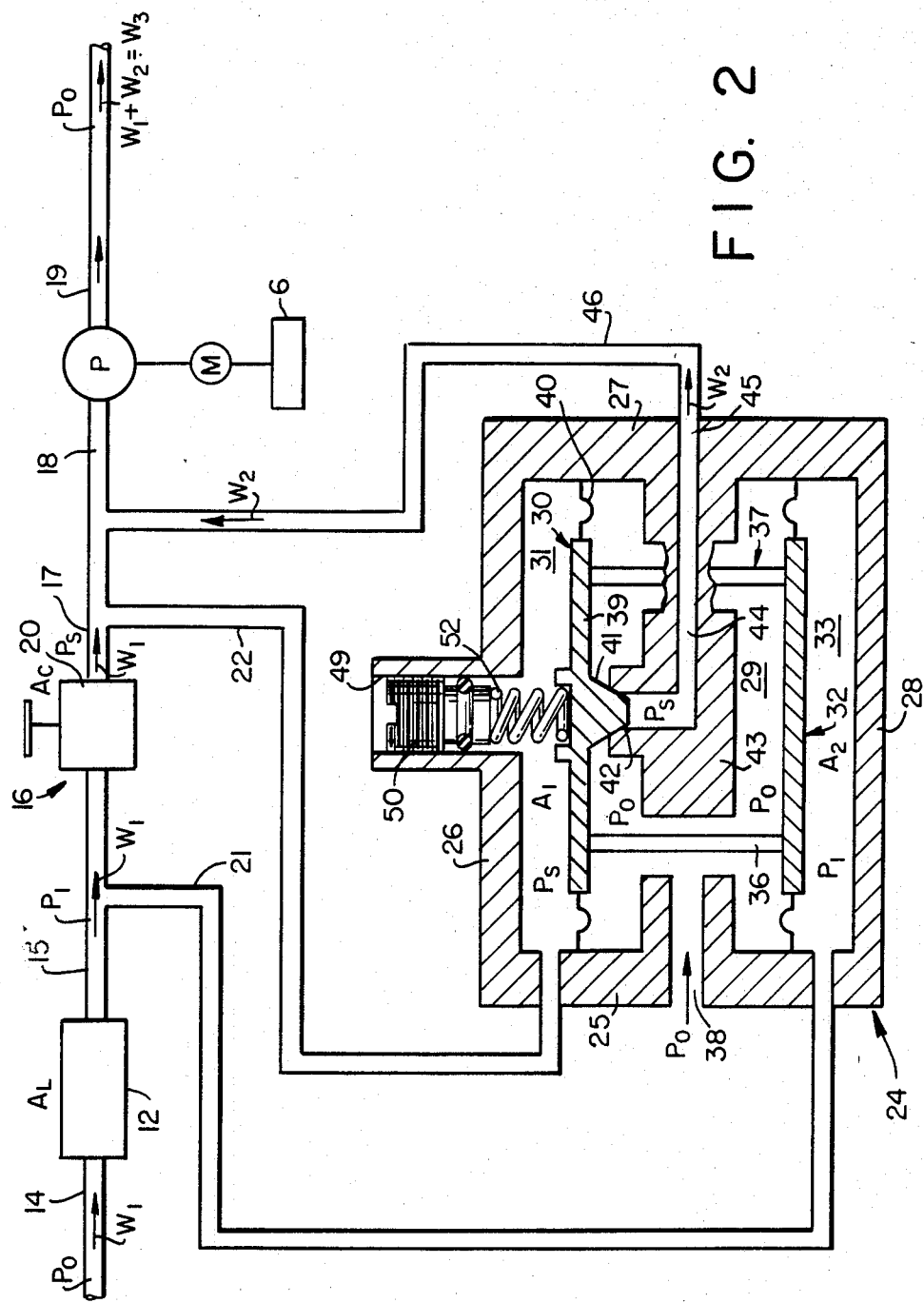
FIG. 2 is a schematic diagram of the gas flow control system embodied in the air sampler of FIG. 1.
Figure 3:
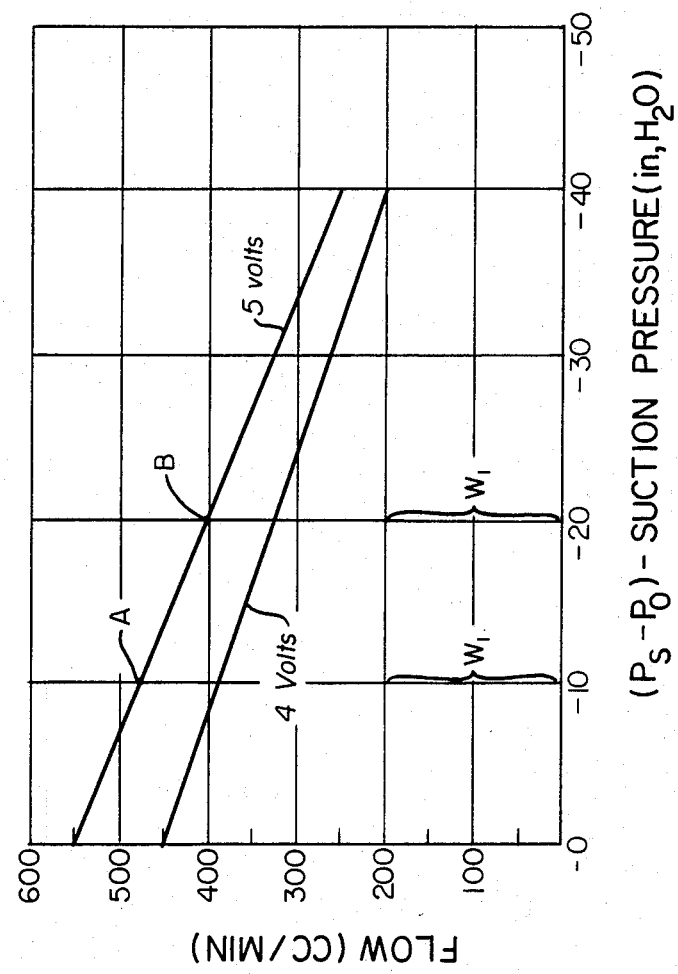
FIG. 3 is a graph of the flow characteristic for the vacuum pump of FIGS. 1 and 2.

Operation of the fluid sampler 10 will now be described in connection with FIGS. 2-4 wherein like reference numerals are used to designate the corresponding components. The test article 12 represents the load (sorbent tube) through which the flow of gas is to be controlled at a preset flow rate. The test article 12 is coupled in series with the vacuum pump P and the manually adjustable control valve 16. In the embodiment of FIG. 2 the inlet end of the test article 12 is coupled to a gas conduit 14 which is open to the atmosphere. Accordingly, the gas drawn through the gas conduit 14 will be air at a pressure Po which is essentially atmospheric pressure.

The outlet end of the test article 12 is coupled through a gas conduit 15 to the manually adjustable flow control valve 16 which in turn is coupled through a gas conduit 17 to the suction end 18 of the vacuum pump P. The discharge end 19 of the pump P is open to the atmosphere. The flow control system of the present invention may also be used in conjunction with a supply reservoir (not shown) of any gaseous environment in place of atmospheric air. In the latter case the discharge end 19 of the pump P would be connected through the reservoir back to the inlet gas conduit 14 in a closed loop.

The manually adjustable flow control valve 16 is a conventional needle valve with an adjustable metering or flow control orifice 20 for establishing a predetermined restriction in the flow line between the gas conduits 15 and 17. Sense lines 21 and 22 are connected to the conduits 15 and 17 for sensing the pressure $P_l$ and $P_s$ in the gas conduits 15 and 17 at opposite sides of the flow control valve 16.

The sense lines 21 and 22 are coupled to the flow controller 24 shown schematically in cross section in FIG. 2. The flow controller 24 in cross-section has four walls 25, 26, 27, and 28 surrounding a central cavity 29. A first diaphragm assembly 30 is suspended between the side walls 25 and 27 for forming a first diaphragm chamber 31 at one end of the central cavity 29 adjacent to the side wall 26. A second diaphragm assembly 32 is suspended between the side walls 25 and 27 at the end of the central cavity 29 opposite the first diaphragm assembly 30. The second diaphragm assembly 32 forms a second diaphragm chamber 33. The sense lines 21 and 22 are connected through openings in the wall 25 to the second and first diaphragm chambers 33 and 31 respectively. Accordingly the pressure in the first diaphragm chamber 31 is equal to the pressure $P_s$ in the gas conduit 17 and the pressure in the second diaphragm chamber 33 is equal to the pressure $P_l$ in the gas conduit 15.

The first and second diaphragm assemblies 30 and 32 are connected together by means of posts 36 and 37 which extend through the central cavity 29. Thus the diaphragm assemblies 30 and 32 move in unison in response to any change in pressure in either the first or second diaphragm chambers 31 and 33 respectively. The wall 25 of the flow controller 24 has a central port 38 which is open to the atmosphere. The central port 38 communicates with the central cavity 29 which pressurizes the central cavity 29 to atmospheric pressure. The first diaphragm assembly 30 includes a pressure plate 39 and a flexible diaphragm 40. The pressure plate 39 has a projecting cone shaped valve poppet 41. The valve poppet 41 is aligned to register with a valve seat 42 formed in a protruding section 43 extending from the wall 27 internal of the central cavity 29. The protruding section 43 has a passageway 44 leading from the valve seat 42 to an exit opening 45 in the wall 27 where it joins a conduit 46. The conduit 46 is connected to the gas conduit 17 at the suction end of the pump P.

The outer wall 26 of the flow controller 24 has a threaded opening 49 in which a manually adjustable screw 50 is engaged. A spring 52 is mounted between the screw 50 and the pressure plate 39 of the diaphragm assembly 30.

The pump P is driven by the DC motor M. The speed of the drive motor M is proportional to the battery supply voltage. The flow envelope characteristic for the pump P is selected to provide the desired operating flow range. For low flow air sampling a vacuum pump P was selected to provide a flow characteristic of 200 cc per minute at a minimum back pressure of 40 inches of water.

In operation the primary flow of air $W_1$ passes through the test load 12 then through the metering orifice 20 of the adjustable control valve 16 from whence it is drawn into the suction side of the pump P. A secondary stream of air $W_2$ is drawn from the flow controller 24 through the conduit 46 and then into the conduit 17 where the secondary stream joins the primary flow of air before entering the suction side of the pump P. The combined flow of air $W_3$ which equals $W_1$ and $W_2$ is discharged by the pump P into the atmosphere.

The difference in pressure ($P_l - P_s$) across the metering orifice 20 of the flow control valve 16 is monitored by the sense lines 21 and 22 which feed into the diaphragm chambers 31 and 33 of the flow controller 24. The theory of operation is to cause the flow controller 24 to reach equilibrium only when the condition $P_l - P_s$ is a predetermined constant value. Thus any change in the absolute value of $P_l$ as a result of a change in load will cause the flow controller 24 to establish a new equilibrium condition with ($P_l - P_s$) constant. This can only be established by varying the flow rate of the secondary stream $W_2$ until the suction pressure $P_s$ at the pump P has varied by an amount corresponding to the change in $P_l$ and the equilibrium condition $P_1 - P_s$ equals a constant is reestablished. On the other hand the primary flow rate $W_1$ will not vary since the condition $P_l - P_s$ also represents the differential pressure across the metering orifice 20. Conversely, the secondary stream $W_2$ will also be varied by the flow controller 24 when there is a dynamic change in the pressure $P_s$ even where the pressure $P_l$ is unchanged until a new equilibrium condition is established with $P_l - P_s$ constant. In each case the primary flow rate $W_1$ will not vary. Stated otherwise for a constant differential pressure $(P_l - P_s)$ the flow $W_1$ through the metering orifice 20 must remain constant assuming there is no change in the density of the gas in the primary flow stream. A change in gas density can also be compensated for by varying the area ratios $A_1$ and $A_2$ of the diaphragm chambers 31 and 33 respectively. The basic equation for flow through an orifice is as follows:

$$W = C_d A_c \sqrt{2g\rho(P_1 - P_s)}$$

where $C_d$, $A_c$, and $\rho$ are constants for a given orifice size and gas. $C_d$ is the coefficient of discharge for the orifice and $A_c$ its area and $g$ is the gravitational unit conversion constant. Accordingly, if the density $\rho$ is constant the flow $W$, will be constant when $(P_l - P_s)$ is constant.

Figure 4:
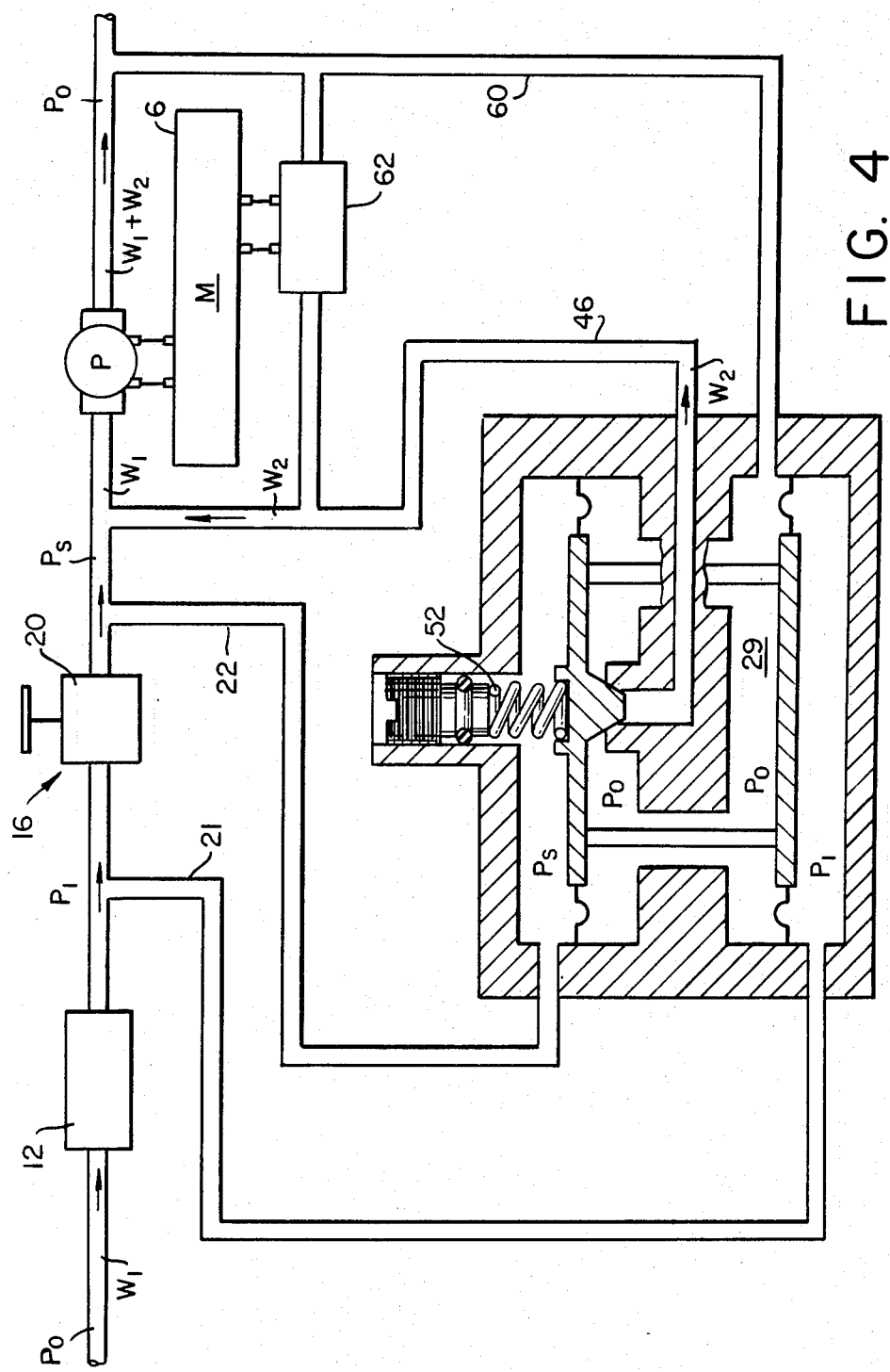
FIG. 4 is a schematic diagram of a slightly modified version of the system of FIG. 2.

Although the primary flow $W_1$ remains constant, the output flow $W_3$, shown only as $W_1 + W_2$ in FIG. 4, from the pump P representing the combined flow $W_1$ and $W_2$ will indeed vary with a change in loading and to an extent determined by the pump flow characteristics. Using the pump flow characteristic curve shown in FIG. 3 a change from operating point A to operating point B on the 5 volt load line due to, e.g., a change in the test article 12 will result in an output flow change from 450 cc per minute at 10 inches of water suction pressure $P_s$ (assume zero gage atmospheric pressure $P_o$) to 400 cc per minute at a back pressure $P_s$ of 20 inches of water. If $W_1$ was 200 cc per minute at operating point A, it still remains 200 cc per minute at operating point B, although $W_2$ varies from 250 to 200 cc per minute.

The absolute value of the suction or back pressure $P_s$ at the vacuum pump P determines for a given load line the new total flow condition $W_3$ drawn by the pump P. Accordingly, the load line characteristic of the pump P need not be linear. The system of the present invention will operate in the same fashion for a decrease in battery voltage which in turn causes a decrease in the speed of the motor M driving the pump P. A drop to the lower load line representing, e.g., a four volt condition, will decrease the total output flow $W_3$ but will not significantly affect the flow $W_1$. The control variable is the secondary flow $W_2$.

Operation of the flow controller 24 which varies the secondary flow $W_2$ to restore an equilibrium condition with $P_l - P_s$ equal to a preset constant is critical to the present invention. The diaphragm assembly 30 has forces acting upon it from the spring 52, the suction pressure $P_s$, the atmosphere pressure $P_o$ in the control cavity 29 and the pressure $P_l$ in the diaphragm chamber 32. The spring force is initially adjusted to establish a desired valve displacement between the valve member 41 and the valve seat 42 for a given differential control pressure $P_l - P_s$. This control pressure $(P_l - P_s)$ provides adjustment for rising, constant, or dropping flow characteristics over the load range. The control orifice setting is used to set the magnitude of primary flow. A change in $P_l$ will as discussed earlier cause a valve unbalance resulting in a new flow condition $W_2$ and a new suction pressure $P_s$ with an equilibrium condition established when $P_l - P_s$ is restored to the constant level originally set up by adjustment of the spring 52. The primary flow $W_1$ will always remain constant at the flow preselected through adjustment of the valve 16.

Although the flow controller 24 is not limited to the use of a valve piston member 41 having a cone shaped geometry this geometry is preferred. The valve seat 42 is preferably of cylindrical geometry. This provides a regulator valve area $$A_v = \left(\frac{\pi d}{2}\right) x$$

where $d$ equals the seat diameter and $x$ equals the displacement of the valve member 41 relative to the valve seat 42. The flow controller is designed to operate in accordance with the following mathematical equation governing control of the regulator:

$$P_1 - P_s = \frac{F_o + K_s x}{A_1 - A_v} + (P_o - P_1)\left(\frac{A_2}{A_1 - A_v} - 1\right)$$

where:
$FV_o$ = initial spring force
$x$ = valve displacement
$P_o$ = ambient discharge pressure
$A_1$ = effective piston area of diaphragm assembly 30
$A_2$ = effective piston area of diaphragm assembly 32

$$A_v = \text{regulator valve area} = \left(\frac{\pi d}{2}\right) x$$

$K_s$ = spring rate

The embodiment of FIG. 4 is essentially identical to that of FIG. 2 and accordingly the same reference numerals have been applied. In FIG. 4 a conduit 60 directly connects the discharge end of the pump P to the central cavity 29 of the flow controller. In addition, a conventional pressure switch 62 is connected across the pump P between the conduits 46 and 60 to shut the pump P down by de-energizing the motor M should the total system pressure, i.e., the pressure across the pump P, become higher than that at which the pump envelope is set. The pressure switch 7 may be coupled through a conventional time delay circuit (not shown) to de-energize the motor M after a suitable time delay has expired. FIG. 4 provides the advantage of a closed loop in the line controller where toxic or other hazardous gases can be sampled without venting to the atmosphere.

Figure 5:
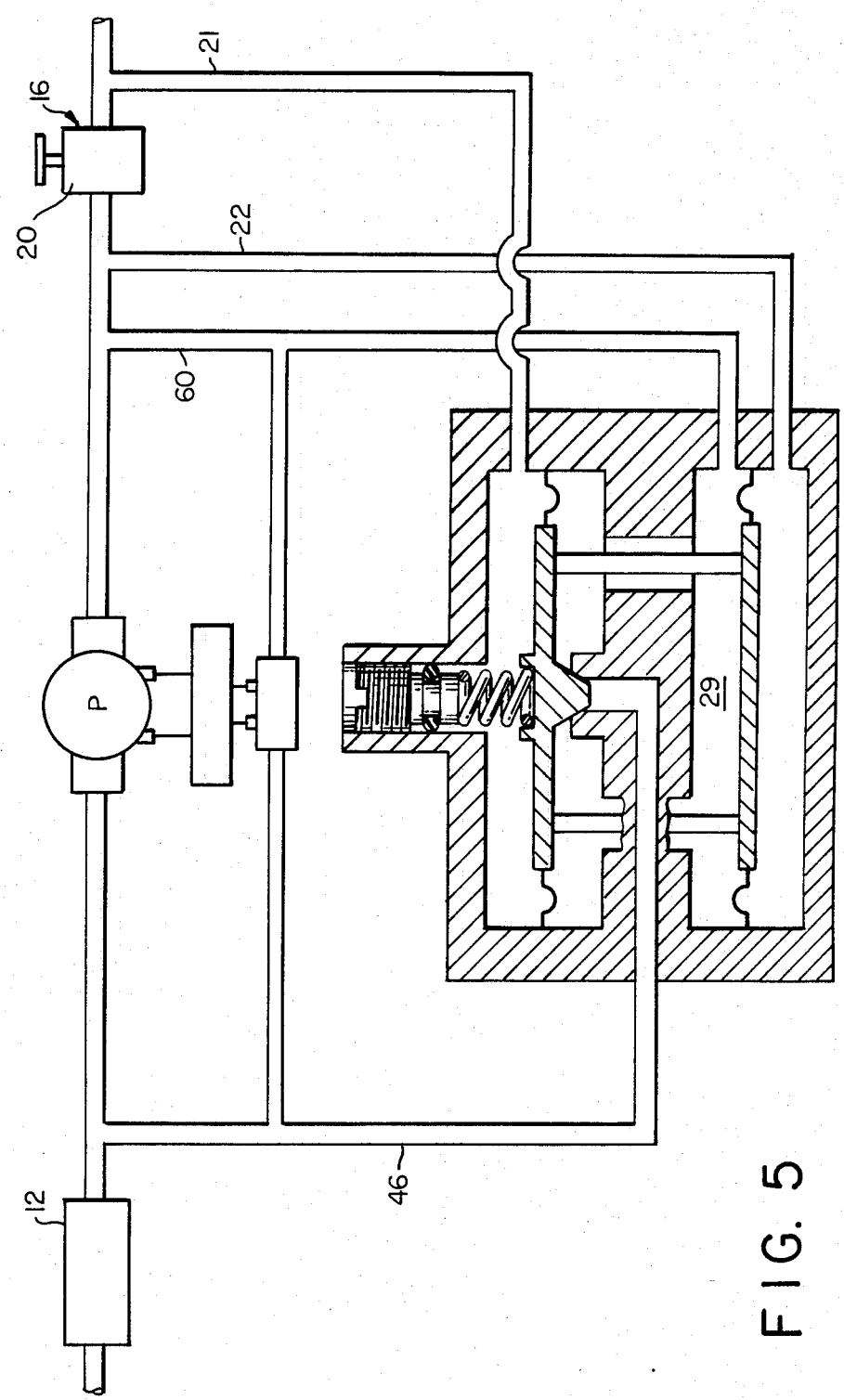
FIG. 5 is a schematic diagram similar to FIG. 4 with the flow control valve on the discharge end of the vacuum pump.

It should be understood that although the test article 12 and flow control valve 16 is shown on the suction side of the pump P this arrangement is not critical to the invention. However, if the flow control valve 16 is placed on the discharge side of the pump P the sense lines 21 and 22 across the flow control valve would have to be reversed in position with respect to the pump P. The FIG. 4 embodiment is in fact preferred over the FIG. 2 embodiment. The test article 12 in FIG. 4 can also be placed on the discharge side of the pump independent of the position of the flow control orifice 16. In the latter case the flow through conduit 60 would be the bypass flow $W_2$ and the pressure in the control chamber 29 would be the pressure on the discharge end 19 of the pump P. The flow through the test article 12 would remain $W_1$. FIG. 5 is similar to FIG. 4 showing the flow control valve 16 on the discharge side of the pump P.

The underlying principle of the invention is the same regardless of which side of the pump the flow control valve 16 is placed or on which side the test article is placed. In each case the pressure across the flow control valve is regulated to a predetermined constant by adjustment of the supplementary flow $W_2$. The supplementary flow $W_2$ is taken from the discharge end of the pump and reintroduced at the suction end of the pump to supplement the primary flow. With the pressure differential across the flow control valve constant the flow $W_1$ will be constant. In the context of this application the use of the expression "maintained constant" is intended to mean regulated to a value having a very close approximation to the initializing condition.

I claim:

1. A fluid sampler for use in sampling a gaseous atmosphere in a collecting device at a constant preselected flow rate comprising: a flow control valve having a manually adjustable flow restricting orifice for preselecting said flow rate; a vacuum pump having a suction end and a discharge end and being connected in series with said flow control valve and the collecting device for drawing gas from the atmosphere through a primary flow line including, in combination, the collecting device, the flow control valve and the pump; means for sensing the pressure differential across said flow control valve; and a flow controller connected across the pump and being responsive to said sensing means for supplying a supplementary flow of gas from the discharge end of the pump into the suction end of the pump such that the flow through the pump equals the combination of the supplementary flow and the primary flow, with the flow controller having valve means for varying said supplementary flow in response to changes in pressure in said sensing means whereby the flow through said collecting device is maintained constant at said preselected flow rate.

2. A fluid sampler as defined in claim 1 wherein said means for sensing the pressure differential across said flow control valve include a first and second sense line.

3. A fluid sampler as defined in claim 2 wherein said flow control valve is connected on the suction side of said vacuum pump.

4. A fluid sampler as defined in claim 2 wherein said flow control valve is connected on the discharge side of said vacuum pump.

5. A fluid sampler as defined in claim 3 or 4 wherein said flow controller comprises a first and second diaphragm assembly forming a first and second diaphragm chamber with said first sense line being connected to said first diaphragm chamber and with said second sense line connected to said second diaphragm chamber; a cavity separating said first and second diaphragm assembly and communicating with the atmosphere; means for connecting said first and second diaphragm assembly for movement in unison in response to a change in pressure in either diaphragm chamber; valve means in communication with said cavity having a valve piston in registration with a valve seat with the displacement of said valve piston relative to said valve seat being a function of the pressure differential in said first and second diaphragm chambers, output means for discharging supplementary gas through said valve means and conduit means for coupling said output means to said primary flow line.

6. A fluid sampler as defined in claim 5 wherein said valve piston is substantially cone shaped.

7. A pneumatic flow control system maintaining a constant rate of gas flow through a load at a preselected flow rate within a wide flow range comprising:
an adjustable metering orifice for preselecting the flow rate for said gas;
a vacuum pump having a suction end and a discharge end for pumping said gas from an ambient source of supply through a primary gas flow line including in combination said load, said adjustable metering orifice and said pump;
means for sensing the difference in pressure across said metering orifice; and
bypass flow means responsive to said sensing means and being connected across said pump for supplying a supplementary flow of said gas from the discharge end of the pump into said primary gas flow line at the suction end of the pump such that the flow through the pump equals the combination of the supplementary flow and the primary flow and means for varying said bypass flow so as to maintain said difference in pressure across the metering orifice constant independent of variations in the load.

8. A pneumatic flow control system as defined in claim 7 wherein said bypass flow means for supplying said supplementary flow of gas comprises a flow controller and wherein said means for sensing the difference in pressure across said metering orifice includes a first and second sense line connected to said flow controller.

9. A pneumatic flow control system as defined in claim 8 wherein said metering orifice is located between said vacuum pump and said load adjacent the suction end of said pump.

10. A pneumatic flow control system as defined in claim 8 wherein said metering orifice is located on the discharge end of said pump with the primary gas flow line forming a series flow path through said load, said pump and said metering orifice.

11. A pneumatic flow control system as defined in claims 9 or 10 wherein said flow controller comprises: a first and second diaphragm assembly disposed on opposite sides of a central cavity for forming a first and second diaphragm chamber with said first sense line being connected to said first diaphragm chamber and with said second sense line being connected to said second diaphragm chamber, an input port connecting said central cavity to ambient pressure at the discharge end of said pump, means for connecting said first and second diaphragm assembly for movement in unison in response to a change in pressure in either diaphragm chamber, valve means having a valve piston in registration with a valve seat with the displacement of said valve piston relative to said valve seat being a function of said pressure differential in said first and second diaphragm chambers, an outlet port for discharging secondary gas through said valve means and conduit means for coupling said outlet port to said primary gas flow line.

12. A pneumatic flow control system as defined in claim 11 wherein said flow controller further includes a spring in engagement with said first diaphragm assembly and means for manually adjusting the force applied by said spring upon said diaphragm assembly for establishing a predetermined pressure differential and wherein said displacement of said valve piston relative to said valve seat is also a function of the spring force.

13. A pneumatic flow control system as defined in claim 12 wherein said valve piston is connected to said first diaphragm assembly and is substantially cone shaped.

14. A pneumatic flow control system as defined in claim 13 further comprising a pressure switch connected across said pump for deactivating said pump when the differential in pressure across said pump exceeds a predetermined pressure corresponding to the pump envelope pressure.

15. A method for maintaining a constant flow of gas from a gaseous atmosphere through a load at a preselected flow rate within a wide flow range comprising:
    drawing said gas from the atmosphere through said load using a vacuum pump having a suction end and a discharge end;
    placing a metering orifice in series with said load and said pump to establish said preselected flow rate;
    sensing the difference in pressure across said metering orifice;
    diverting flow from the discharge end of said vacuum pump to form a secondary flow of said gas;
    inserting said secondary flow into the suction end of said pump such that it combines with the gas flow through said load before passing into said pump; and
    adjusting the flow rate of said secondary flow in response to a change in load to maintain said difference in pressure substantially constant whereby the flow through the load will be substantially held at the preselected flow rate independent of the change in load.

16. A method as defined in claim 15 wherein said metering orifice is placed on the suction end of the pump between the load and the pump.

17. A method as defined in claim 15 wherein said metering orifice is placed on the discharge end of the pump.

* * * * *